United States Patent [19]

Pelzer et al.

[11] Patent Number: 5,703,123
[45] Date of Patent: Dec. 30, 1997

[54] METHOD FOR CAUSING A PHYSIOLOGICAL COOLING EFFECT TO THE SKIN OR MUCOSA INVOLVING THE APPLICATION OF CARBONIC ACID ESTERS

[75] Inventors: Ralf Pelzer, Fuerstenberg; Horst Surburg; Rudolf Hopp, both of Holzminden, all of Germany

[73] Assignee: Haarmann & Reimer GmbH, Holzminden, Germany

[21] Appl. No.: 509,443

[22] Filed: Jul. 31, 1995

Related U.S. Application Data

[60] Continuation of Ser. No. 319,349, Oct. 6, 1994, abandoned, which is a division of Ser. No. 99,786, Jul. 30, 1993, abandoned.

[30] Foreign Application Priority Data

Aug. 6, 1992 [DE] Germany ............... 42 26 043.4

[51] Int. Cl.$^6$ ............................................. A61K 31/265
[52] U.S. Cl. ............................................. 514/512; 558/276
[58] Field of Search ............................................. 514/512

[56] References Cited

U.S. PATENT DOCUMENTS 3,419,543  12/1968  Mold et al. ............... 558/276 X
4,044,120  8/1977  Rowsell et al. ............... 424/48

*Primary Examiner*—Michael G. Ambrose
*Attorney, Agent, or Firm*—Sprung Kramer Schaefer & Briscoe

[57] ABSTRACT

Asymmetric carbonates, thiocarbonates and urethanes having a physiological cooling effect on the skin and on mucosae are described.

5 Claims, No Drawings

METHOD FOR CAUSING A PHYSIOLOGICAL COOLING EFFECT TO THE SKIN OR MUCOSA INVOLVING THE APPLICATION OF CARBONIC ACID ESTERS

This application is a continuation of application Ser. No. 08/319,349, filed on Oct. 6, 1994, now abandoned, which is a division of application Ser. No. 08/099,786, filed on Jul. 30, 1993, now abandoned.

The invention relates to agents without a troublesome characteristic smell and characteristic taste which, when applied to the skin or to the mucosae, cause a physiological cooling effect. The action, which gives to the person affected the impression of freshness, evidently arises due to stimulation of the corresponding receptors of the human nervous system. The invention furthermore relates to new compounds which can cause this action.

The best known naturally occurring compound having a physiological cooling action is without doubt the (–)-menthol which occurs in peppermint oil (ex *Mentha arvensis*). It is used, for example, for preparation of tooth cleaning agents, mouthwashes, foodstuffs, drinks and cosmetics. However, the typical intense characteristic peppermint aroma and the characteristic bitter-burning taste are often found to be unpleasant.

The N-acetylglycine menthyl ester proposed in German Offenlegungsschrift 2 433 165 and the menthol esters of heterocyclic carborylic acids proposed in German Offenlegnngsschrift 2 339 661 are bitter, and the menthyl keto esters proposed in U.S. Pat. No. 3,830,930 are in some cases persistently bitter and have only a weak cooling action.

Menthol esters of naturally occurring $C_2$–$C_6$-hydroxycarboxylic acids (which are in turn optionally esterified by $C_1$–$C_4$-carboxylic acids on the hydroxyl group) which have no smell or taste and have a long-lasting cooling action are known from German Offenlegungsschrift 2 608 226. 1-Menthyl lactate, in particular, has proved itself in practice. Nevertheless, the product is not stable to bases, so that it is not suitable for all applications (for example soaps).

Other products have also already been used in practice, for example 3-1-menthoxypropane-1,2-diol (European Patent Specification 80 148) and N-ethyl-p-menthane-3-carbox-amide (German Offenlegungsschrift 2 205 255 and 2 413 639).

1-Menthanyl ethyl carbonate is proposed as a cooling agent in German Offenlegungsschrift 2 022 369. This substance has a distinctly fruity orange-like, somewhat woody characteristic smell. Comparedwith 1-menthol, the cooling action is quite considerably weaker not only in the pure form, but above all in media such as, for example, a fondant mixture. However, there is a greatly increasing demand for agents which have a cooling action which as far as possible reaches or exceeds menthol in intensity, coupled with the absence of a characteristic smell and characteristic taste.

Surprisingly, it has now been found that mixed carbonic acid derivates which have free polar groupings, in contrast to those without these free polar groupings, have a cooling effect which is in some cases greater than that of menthol, and at the same time substantially neutral in taste and smell.

The invention relates to agents having a physiological cooling effect which comprise at least one compound of the formula

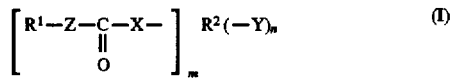

wherein $R^1$ denotes $C_4$–$C_{20}$-alkyl, $C_5$–$C_{20}$-cycloalkyl or -heterocycloalkyl or $C_5$–$C_{20}$-alkoxy, $C_6$–$C_{12}$-aryl, $C_5$–$C_{10}$-heteroaryl or $C_7$–$C_{11}$-aralkyl, $R^2$ denotes an m+w·n-valent aliphatic $C_1$–$C_8$ radical, a cycloaliphatic or heterocycloaliphatic $C_3$–$C_{15}$ radical or an araliphatic $C_7$–$C_{20}$ radical or an alkoxy- or acyloxy-containing aliphatic $C_3$–$C_{15}$ radical, Z and X independently of one another denote —O—, —S— or —NH—, Y denotes hydroxyl, $C_1$–$C_{10}$-alkoxy, $C_2$–$C_6$-acyloxy, amino, mercapto or —O—$R^3$—O—, $R^3$ denotes $C_1$–$C_6$-alkylene, w denotes the valency of the radical Y, preferably 1 or 2, and m and n independently of one another denote integers from 1 to 8, with the proviso that the sum of m+n is not more than 12.

Preferred radicals $R^1$ include $C_1$–$C_3$-substituted cyclohexyl, preferably menthan-3-yl, and branched $C_3$–$C_8$-alkyl radicals.

Preferred radicals $R^2$ include, for example, ethylene, propylene, $CH_3$—$C(CH_2$—$)_3$, $CH_3CH_2C(CH_2$—$)_3$, $C(CH_2$—$)_4$ and trivalent $C_6$-hydrocarbon radicals.

Preferred compounds I include, in particular, the compounds

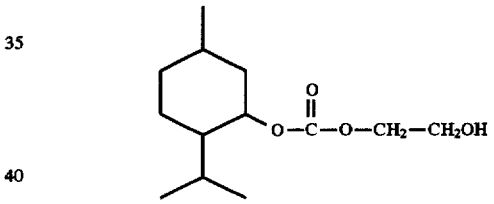

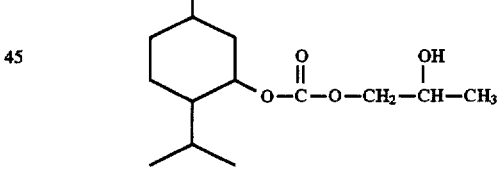

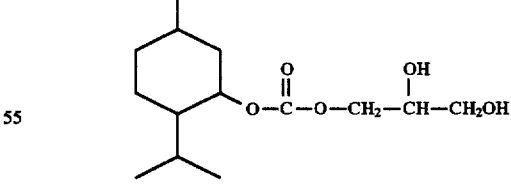

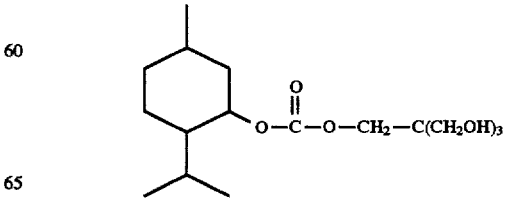

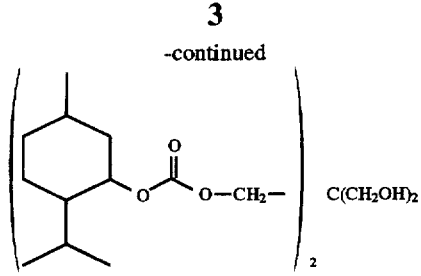 C(CH$_2$OH)$_2$

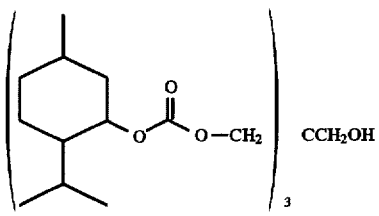 CCH$_2$OH

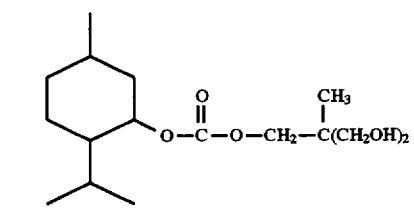

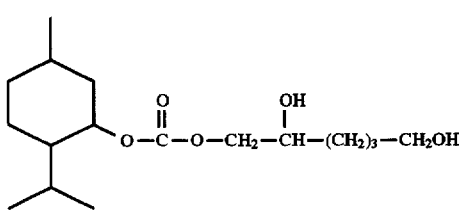

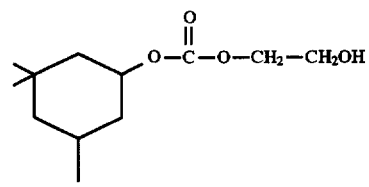

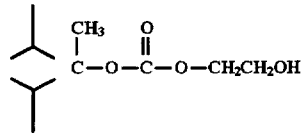

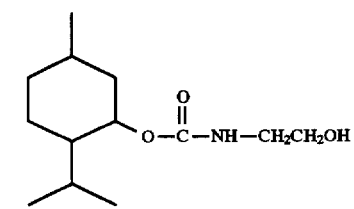

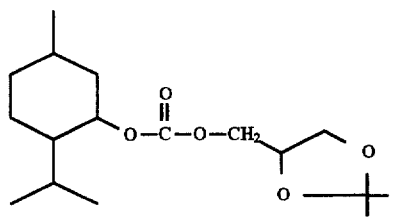

Compounds of the formula

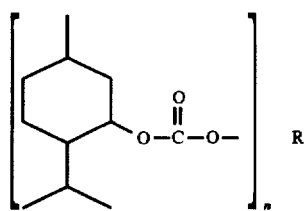

wherein n depends on the nature of the radical R and R denotes the radical of a mono-, di-, tri- or polysaccharide or of a glycol (obtained by removal of at least one hydroxyl group) are known from U.S. Patent Specification 3 419 543. The compounds are recommended as tobacco additives and are said to decompose in the burning tobacco so that menthol is released. A physiological cooling action of the non-decomposed compounds themselves is neither disclosed nor suggested.

The other compounds of the formula I are new. The invention thus furthermore relates to the compounds I, excluding the compounds known from U.S. Pat. No. 3,419, 543.

The compounds I can be prepared by base-controlled reaction of chloroformic acid esters with the corresponding alcohols, amines or thiols or by a staggered reaction of phosgene, diphosgene, triphosgene or comparable active carbonic acid derivatives with an R$^1$-alcohol -amine or -thiol on the one hand and the corresponding R$_2$-alcohols, -amines or -thiols on the other hand. The reaction will preferably be carried out in equimolar ratios, but if appropriate also with one component in excess. Suitable bases for the reaction are organic amines, such as pyridine or trialkylamines or inorganic bases such as NaOH, KOH or Na$_2$CO$_3$.

The compounds (I) have asymmetric C atoms in some cases; optical isomerism can therefore occur in these compounds. They can be in the form of mixtures of the optical isomers or in the form of pure isomers, depending on the starting material and the preparation methods used. The cooling action of the isomers may differ, so that one or other of the isomers may be preferred.

The compounds I according to the invention are preferably also used in combination with menthol and/or other known cooling substances of the kind mentioned in the patents referred to on page 2, in order to considerably prolong and/or enhance the poor cooling effect displayed by some of them. It is also advantageous to combine natural, nature-identical or synthetic aroma compositions, in particular of the mint type, with compounds I, in order to enhance their cooling effect and impression of freshness.

The agents according to the invention can contain carriers and/or diluents, in addition to the compounds I. The nature thereof depends on the intended purpose of the agent.

The agents according to the invention can be used in all instances where a physiological cooling action is desirable. Compositions in which such cooling agents are popularly used are, for example:

foodstuffs:
   patisserie products, confectionery, sweet foods (sweets, chocolates), waffle fat compositions, alcoholic drinks (beers, spirits, liqueurs), non-alcoholic drinks (fruit juices, lemonades, cola, milk drinks, mineral water, water-soluble tablets), milk products, yoghurts, icecream products, chewing gum, jelly products, marmelades, jams and desserts;

cosmetic agents:
   shaving creams, foams, gels and soaps; after-shave products with or without any alcohol contents, such as lotions, milks, creams, gels and balms; pre-shave products such as lotions, milks, creams, gels and balms; skin-care products such as creams, lotions, milks, gels, foams and oils; skin-cleansing products such as creams, lotions, tonics, tissues and pads; skin-freshening products such as gels, lotions, and tissue wipes; perfumes such as eaux de cologne, eaux de toilette, eaux de parfum, extracts and splash colognes; deodorants and antiperspirant products such as stacks, roll-ons, sprays, creams and powders; after-sun products, such as lotions, balms, milks, gels, creams, sprays, shower gels and shampoos; lip-care products such as sticks and pomades, hair-removing products such as creams, milks and foams, face masks, sports products such as oils, tonics, milks, creams gels, sprays and balms; hair-cleaning and hair-care products such as shampoos, rinses, conditioners, tonics, pomades, oils, gels, creams, balms, dyes, perms; soaps such as toilet soaps and liquid soaps; bath products such as oils and foam baths; talcum powders; foot-care products such as footbaths, creams, tonics, gels, milks, sprays; skin massage products such as oils, creams, lotions, milks and sprays; mouth and dental care products such as toothpastes, tooth gels, mouthwashes, mouth sprays, gargling preparations, toothpicks, dental floss, denture-cleaning agents, water picks and chewing-gums;

tobacco goods:

cigarettes, cigars, chewing tobacco, snuff, pipe tobacco, filter tips;

household products:

hand washing-up liquids, fabric softeners, fabric impregnating agents, toilet paper, air fresheners and straws;

pharmaceutical preparations:

antiseptic ointments, antiacids for stomach disorders, liniments, oral analgesics, cough mixtures, throat lozenges and dental rinses;

textile-treatment agents:

washing agents, fabric softeners, finishing agents.

The end products contain the compounds I in an amount which is sufficient to bring about the desired sensation of cold. As a rule, 0.01 to 3, preferably 0.05 to 1, percent by weight, based on the weight of the total composition, are used.

The following examples illustrate the invention. The percentage data are percentages by weight, unless stated otherwise.

EXAMPLES

Example 1

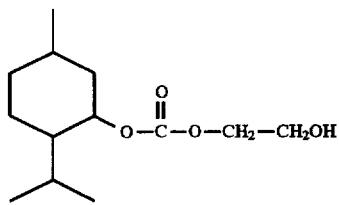

62 g (1 mol) of ethylene glycol and 48 g (0.6 mol) of pyridine are initially introduced into a 1000 ml three-necked flask. 109 g (0.5 mol) of menthyl chloroformate are metered in over a period of 2 hours. The reaction is distinctly exothermic and reaches almost 50° C. at times. The mixture is subsequently stirred at 60° C. for 2 hours. It is acidified to pH=2 with concentrated hydrochloric acid (about 70 g of HCl), the reaction temperature being kept at about 30° C. by cooling. After separation of the phases, the aqueous phase is extracted with 50 ml of ether and the combined organic phases are concentrated. 300 ml of hexane are added to the residue, most of the product crystallising out (52 g). The mother liquor which remains is distilled and, at a boiling point of 137°–143° C. (0.2 mbar), gives 27 g of distillate, which is crystallised by washing with hexane.

The purified crystals have a melting point of 51.4° to 51.5° C. and an optical rotation of $\alpha^{20}_D = -67.2°$ (10% strength in ethanol).

Example 2

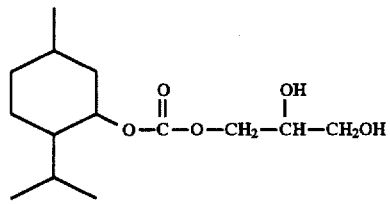

Process analogous to Example 1, from 54.5 g (0.25 mol) of menthyl chloroformate and 92.1 g (1 mol) of glycerol. The reaction mixture comprises the desired compound to the extent of 91.3% and has the following properties:

$D^{25}_{25}=1.0750$; $n^{20}_D=1.4720$; $\alpha^{25}_D=-59.60°$ (10% strength in ethanol). Yield: 73.4% of theory, based on the menthyl chloroformate.

Example 3

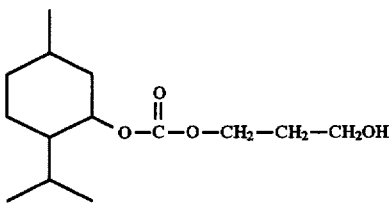

Process analogous to Example 1, from 109 g (0.5 mol) of menthyl chloroformate and 76.1 g (1 mol) of propane-1,3-diol; isolation by distillation.

$D^{25}_{25}=1.0218$; $n^{20}_D=1.4615$; $\alpha^{25}_D=-64.8°$ (10% strength in ethanol). Yield: 63.1% of theory, based on the menthyl chloroformate.

Example 4

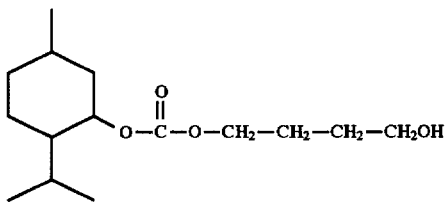

Process analogous to Example 1, from 100 g (0.46 mol) of menthyl chloroformate and 49.6 g (0.55 mol) of butane-1,4-diol; isolation by distillation.

$D^{25}_{25}=1.0111$; $n^{20}_D=1.4621$; $\alpha^{25}_D=-58.5°$ (10% strength in ethanol). Yield: 51.4% of theory, based on the menthyl chloroformate.

Example 5

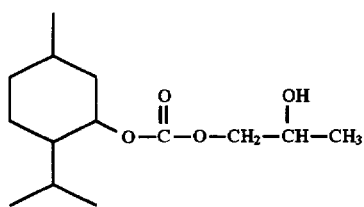

Process analogous to Example 1, from 100 g (0.46 mol) of menthyl chloroformate and 42 g (0.55 mol) of propane-1,2-diol; purification by distillation.

The distillate (130 g) comprises the desired compound to the extent of 89.1% and has the following properties:

$D^{25}_{25}$=1.0154; $n^{20}_D$=1.4578; $\alpha^{25}_D$=−62.2° (10% strength in ethanol). Yield: 82.1% of theory, based on the menthyl chloroformate.

Example 6

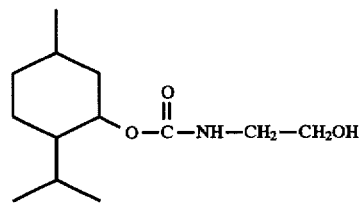

92 g (1.5 mol) of ethanolamine in 200 ml of methyl tert-butyl ether (MTBE) are initially introduced into a 1000 ml three-necked flask. 109 g (0.5 mol) of menthyl chloroformate are metered in initially at room temperature, without cooling, a distinct increase in temperature occurring, and the mixture is subsequently stirred at 55° C. for 3 hours.

100 ml of water are added to the two-phase, crystalline/slurry-like reaction mixture, the phases are separated, the aqueous phase is extracted twice with MTBE (100 ml each time) and the combined MTBE phases are concentrated on a rotary evaporator. 124 g of white crystals which are 97.5% pure are obtained. Distillation (boiling point 140° C./0.1 mbar) gives the pure product; melting point 77.8° to 78.6° C.; $\alpha^{20}_D$=−66.3° (10% strength in ethanol).

Example 7

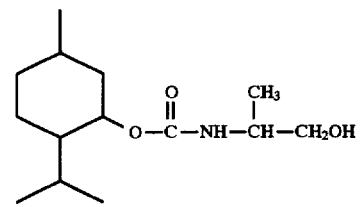

Process analogous to Example 6, from 100 g (0.46 mol) of menthyl chloroformate and 82.6 g (1.1 mol) of 2-aminopropan-1-ol. Yield: 96.6% of theory, based on the menthyl chloroformate. Melting point 72°–72.5° C.; $\alpha^{20}_D$= −63.3° (10% strength in ethanol).

Example 8

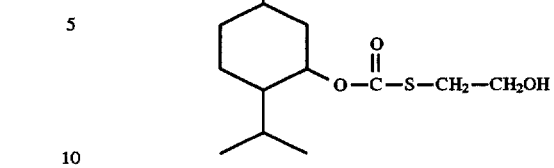

Process analogous to Example 1, from 100 g (0.46 mol) of menthyl chloroformate and 43 g (0.55 mol) of monothioethylene glycol. Distillation (boiling point 130.4°–133.7° C./0.3 mbar) gives a mixture (49% of theory, based on the menthyl chloroformate) of ⅔ of the desired compound and ⅓ of the compound

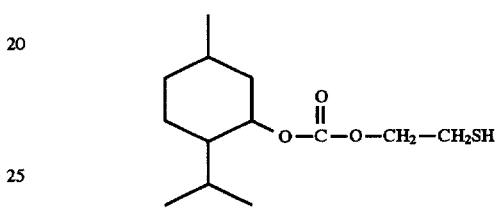

$D^{25}_{25}$=1.0483; $n^{25}_D$=1.4870; $\alpha^{20}_D$=−62.5° (10% strength in ethanol).

Example 9

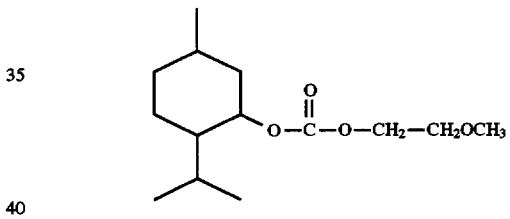

Preparation analogous to Example 1, from 100 g (0.46 mol) of menthyl chloroformate and 42 g (0.55 mol) of 2-methoxyethanol; isolation by distillation (boiling point 125° to 130° C./0.2 mbar) without subsequent crystallisation from hexane. A yield of 93.4% of theory, based on the menthyl chloroformate, is obtained.

$D^{25}_{25}$=0.9949; $n^{25}_D$=1.4499; $\alpha^{20}_D$=−62.5° (10% strength in ethanol).

Example 10

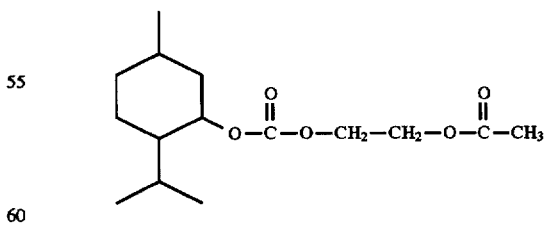

Process analogous to Example 1, from 100 g (0.46 mol) of menthyl chloroformate and 57.2 g (0.55 mol) of ethylene glycol monoacetate. Distillation (boiling point 120°–120.5° C./0.2 mbar) gives 80.1 g of the desired compound.

$D^{25}_{25}$=1.0411; $n^{25}_D$=1.4530; $\alpha^{20}_D$=−56.2° (10% strength in ethanol).

Example 11

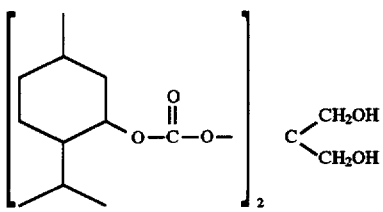

Preparation analogous to Example 1, from 109 g (0.5 mol) of menthyl chloroformate and 136 g (1 mol) of pentaerythritol in the presence of 79.9 g (1.01 mol) of pyridine; a mixture of the mono-, di- and tricarbonate is obtained. The dicarbonate has the strongest cooling action. The mixture has the following properties:

$n^{20}_D = 1.4739$; $\alpha^{20}_D = -50°$ (10% strength in ethanol).

Example 12

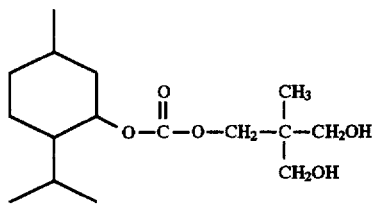

Process analogous to Example 11, from 109 g (0.5 mol) of menthyl chloroformate and 120 g (1 mol) of 2,2,2-trimethylolethane in the presence of 79.9 g (1.01 mol) of pyridine; distillation gives 73% of theory, based on the menthyl chloroformate, of the desired product.

$n^{20}_D = 1.4742$; $\alpha^{20}_D = -56.8°$ (10% strength in ethanol).

Example 13

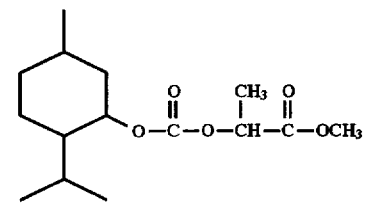

65 g (0.55 mol) of ethyl lactate are initially introduced into 400 ml of MTBE, 43.5 g (0.55 mol) of pyridine are added, 100 g (0.46 mol) of menthyl chloroformate are added dropwise in the course of 2.5 hours, and the mixture is after-reacted at room temperature for a further 2 hours.

The pyridinium hydrochloride formed is dissolved in 100 ml of water. The organic phase is washed in each case once with 10% strength hydrochloric acid, concentrated aqueous sodium bicarbonate solution and with water. Fractional distillation (boiling point 130.4°–135.7° C./1.5 mbar) gives 84.4% of theory, based on the menthyl chloroformate, of the desired product.

$D^{25}_{25} = 1.0167$; $n^{20}_D = 1.4480$; $\alpha^{20}_D = -71.5°$ (10% strength in ethanol).

Example 14

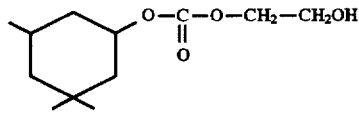

600 ml of hexane are initially introduced into the reaction vessel with 119 g (0.4 mol) of triphosgene; 142 g (1 mol) of 3,3,5-trimethylcyclohexanol and 79 g (1 mol) of pyridine are dissolved in 200 ml of hexane and the solution is added dropwise at room temperature in the course of about 2 hours. After an after-reaction time of 12 hours, a mixture of 62 g (1 mol) of ethylene glycol, 79 g (1 mol) of pyridine and 100 ml of hexane is added dropwise, and once more an after-reaction for 12 hours follows. The mixture is stirred with 250 ml of water to dissolve the pyridinium hydrochloride which has precipitated, the phases are separated and the organic phase is washed once with 100 ml of 10% strength hydrochloric acid, once with 100 ml of 10% strength aqueous $NaHCO_3$ solution and twice with 100 ml of water.

Fractional distillation gives the product in the boiling range of 112°–113° C. under 0.5 mbar.

$D^{25}_{25} = 1.0463$; $n^{20}_D = 1.4578$ Yield: 46.3 % of theory.

We claim:

1. A method for causing a physiological cooling effect to the skin or mucosa, which comprises applying to the skin or mucosa at least one compound of the formula

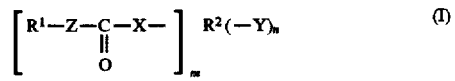

wherein

R¹ denotes $C_4$–$C_{20}$-alkyl, $C_5$–$C_{20}$-cycloalkyl or -heterocycloalkyl or $C_5$–$C_{20}$-alkoxy, $C_6$–$C_{12}$-aryl, $C_5$–$C_{10}$-heteroaryl or $C_7$–$C_{11}$-aralkyl, R² denotes an m+w·n-valent aliphatic $C_1$–$C_8$ radical, a cycloaliphatic or heterocycloaliphatic $C_3$–$C_{15}$ radical or an araliphatic $C_7$–$C_{20}$ radical or an alkoxy- or acyloxy-containing aliphatic $C_3$–$C_{15}$ radical, Z and X each denote —O—, Y denotes hydroxyl, $C_1$–$C_{10}$-alkoxy, $C_2$–$C_6$-acyloxy, amino, mercapto or —O—R³—O—, R³ denotes $C_1$–$C_6$-alkylene, w denotes The valency of the radical Y and m and n independently of one another denote integers from 1 to 8, with the proviso that the sum of m+n is not more than 12.

2. The method of claim 1, wherein m and n each denote 1,

R¹ denotes $C_1$–$C_3$-substituted cyclohexyl,

R² denotes an aliphatic $C_1$–$C_8$ radical, an alkoxy- or acyloxy- containing aliphatic $C_3$–$C_{15}$ radical, Z and X denote —O—, and Y denotes hydroxyl, $C_1$–$C_{10}$-alkoxy, or $C_2$–$C_8$-acyloxy.

3. The method of claim 1, wherein said compound is a member of the group consisting of

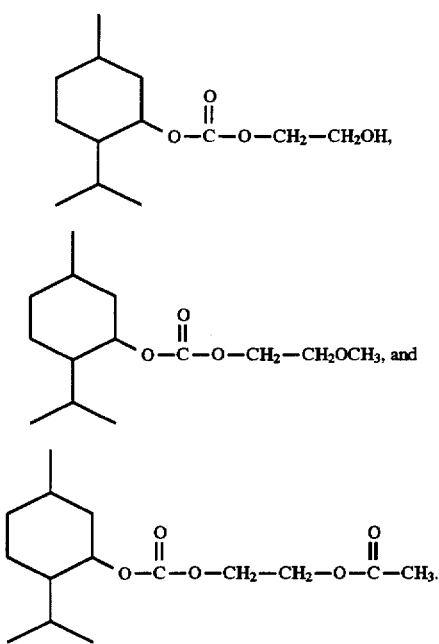
4. The method of claim 1, wherein said compound is
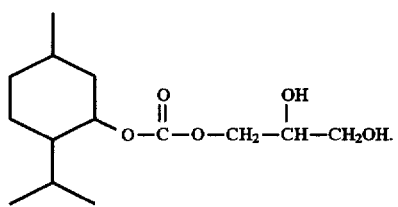
5. The method of claim 1, wherein said compound is
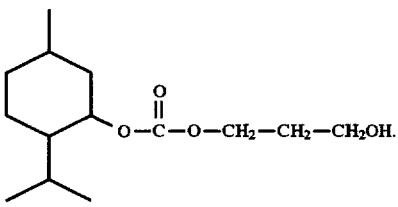
* * * * *